(12) United States Patent
Chodorowski-Kimmes et al.

(10) Patent No.: US 8,722,025 B2
(45) Date of Patent: May 13, 2014

(54) COSMETIC DERMATOLOGICAL COMPOSITION, COSMETIC TREATMENT METHOD, AND HYALURONIC ACID DERIVATIVE

(75) Inventors: Sandrine Chodorowski-Kimmes, Senlis (FR); Maria Dalko, Versailles (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/520,426

(22) PCT Filed: Dec. 14, 2010

(86) PCT No.: PCT/FR2010/052713
§ 371 (c)(1),
(2), (4) Date: Aug. 1, 2012

(87) PCT Pub. No.: WO2011/080450
PCT Pub. Date: Jul. 7, 2011

(65) Prior Publication Data
US 2013/0017164 A1    Jan. 17, 2013

Related U.S. Application Data

(60) Provisional application No. 61/301,344, filed on Feb. 4, 2010.

(30) Foreign Application Priority Data

Jan. 4, 2010  (FR) ..................................... 10 50010

(51) Int. Cl.
| | | |
|---|---|---|
| *A61K 8/73* | (2006.01) | |
| *A61Q 3/00* | (2006.01) | |
| *A61Q 1/10* | (2006.01) | |
| *A61Q 9/04* | (2006.01) | |
| *A61Q 7/00* | (2006.01) | |
| *A61Q 5/02* | (2006.01) | |
| *A61Q 5/06* | (2006.01) | |
| *A61Q 1/00* | (2006.01) | |
| *C08B 37/08* | (2006.01) | |

(52) U.S. Cl.
USPC ........... 424/61; 424/63; 424/70.13; 424/70.2; 424/70.7; 424/73; 510/119; 510/151; 510/158; 514/54; 536/53

(58) Field of Classification Search
None
See application file for complete search history.

(56) References Cited

U.S. PATENT DOCUMENTS

2009/0088396 A1*  4/2009  Asam .............................. 514/33

FOREIGN PATENT DOCUMENTS

| WO | WO-99/56799 A1 | 11/1999 |
| WO | WO-00/16818 A1 | 3/2000 |
| WO | WO-00/27887 A2 | 5/2000 |

* cited by examiner

*Primary Examiner* — Robert A Wax
*Assistant Examiner* — Randeep Singh
(74) *Attorney, Agent, or Firm* — Novak Druce Connolly Bove + Quigg LLP

(57) ABSTRACT

The invention relates to a cosmetic or dermatological composition comprising a hyaluronic acid derivative which comprises ureidopyrimidone units, to the said derivatives and to a cosmetic treatment method using them.

24 Claims, No Drawings

COSMETIC DERMATOLOGICAL COMPOSITION, COSMETIC TREATMENT METHOD, AND HYALURONIC ACID DERIVATIVE

CROSS REFERENCE TO RELATED APPLICATIONS

This application is a National Phase filing under 35 U.S.C. §371 of PCT/FR2010/052713 filed on Dec. 14, 2010; and this application claims priority to Application No. 1050010 filed in France on Jan. 4, 2010, and this application claims the benefit of U.S. Provisional Application No. 61/301,344 filed on Feb. 4, 2010, under 35 U.S.C. §119; the entire contents of all are hereby incorporated by reference.

The present invention relates to a cosmetic or dermatological composition comprising functionalized derivatives prepared from hyaluronic acid and to a cosmetic treatment method employing the said composition.

Women and men currently have a tendency to wish to appear young for as long as possible and consequently wish to soften the signs of ageing of the skin, such as loss of firmness, of elasticity, of tonicity and/or of suppleness, which are reflected in particular by wrinkles and fine lines. On this subject, advertising and fashion give instances of products intended to retain radiant and wrinkle-free skin for as long as possible, these being signs of youthful skin, all the more so as the physical appearance affects the mind and/or the morale.

Human skin is composed of two compartments, namely a surface compartment, the epidermis, and a deep compartment, the dermis.

The epidermis is in contact with the external environment. Its role consists in protecting the body from dehydration and external attacks, whether chemical, mechanical, physical or infectious. The natural human epidermis is composed mainly of three types of cells: keratinocytes, which form the vast majority, melanocytes and Langerhans' cells. Each of these cell types contributes by its specific functions to the essential role played by the skin in the body.

The dermis provides the epidermis with a solid support. It is also its source of nutrients. It is mainly composed of fibroblasts and of an extracellular matrix. It also comprises leukocytes, mast cells or tissue macrophages. It is also traversed by blood vessels and nerve fibres.

The extracellular matrix of the dermis is composed of proteins belonging to several main families: collagens, matrix glycoproteins other than collagens (fibronectin, laminin), elastin, proteoglycans and glycosaminoglycans (GAGs) in the free form (that is to say, not bonded to a protein), including hyaluronic acid. These proteins are predominantly synthesized by fibroblasts and it is known that the skin ageing process brings about a decline in these metabolic activities, resulting in a decrease in the proteins of the extracellular matrix of the dermis, and a decrease in cell growth, resulting in a detrimental change in the mechanical properties of the skin, in particular its firmness, its elasticity, its tonicity and/or its suppleness.

Skin ageing is a natural physiological process; it is not regarded as a pathological condition or a therapeutic disorder.

The main clinical signs of skin ageing are in particular the appearance of fine lines and wrinkles, which increase with age. These wrinkles can be deep, moderate or superficial, and they affect in particular the nasolabial folds, the periorbital region, the outline of the lips and the forehead (glabellar lines); these wrinkles and fine lines are reflected by a depression or folds at the surface of the skin.

Different methods have been proposed for combating wrinkles and fine lines, including the use of skin care products comprising cosmetic active agents (antiwrinkle, moisturizing or tightening active agents, in particular). To this end, hyaluronic acid has been proposed as active agent capable of being used in numerous cosmetic applications, in particular as antiageing active agent. It also plays an important role in the moisturizing and elasticity of the skin. The hyaluronic acid used in cosmetic formulations is generally provided in the form of sodium hyaluronate. In order to increase its effectiveness, provision has also been made to use it in injection, by mesotherapy, or as product for filling in wrinkles.

However, it has been found that this active agent has a limited lifetime on the skin but very particularly when it is injected. This is because hyaluronidases are enzymes present in the skin which decompose hyaluronic acid and thus reduce the impact thereof in cosmetic compositions. The decomposition of hyaluronic acid takes place by virtue of the combined action of three different hyaluronidases. The half-life of hyaluronic acid, due to the very rapid catabolism of the molecule, varies from one tissue to another; by way of indication, it is approximately one day at the dermis and epidermis.

Due to its short half-life, provision has been made to crosslink hyaluronic acid. The crosslinking can be carried out in an alkaline medium, using the carboxyl and hydroxyl sites of the molecule. However, this crosslinking can also be carried out in an acidic medium, although the bonds created in this medium are markedly weaker than those created in an alkaline medium. The crosslinking process does not change the polyanionic nature of the polysaccharide but substantially reduces the miscibility with water of the gel obtained. Mention may be made, among the various crosslinking agents capable of being used, of divinyl sulphone, 1,2,7,8-diepoxyoctane and 1,4-butanediol diglycidyl ether.

However, in some cases, it may be preferable to have available noncrosslinked hyaluronic acid, in particular when it is planned to inject it, for example into the epidermis, or to employ it by mesotherapy; however, it is also desirable for it to be, all the same, resistant to enzymatic decomposition. It has been found that the chemical modifications can affect the physicochemical characteristics and the biological properties of hyaluronic acid, and its evolution after application; furthermore, the half-life of hyaluronic acid derivatives, and thus their bioavailability, still remains too short.

The aim of the present invention is to provide compounds derived from hyaluronic acid which may be crosslinked or noncrosslinked but which exhibit good resistance to enzymatic decomposition.

These derivatives have a very particular application in cosmetic compositions, making it possible to prevent and/or reduce the effects of ageing and/or to restore the mechanical properties of the skin, such as its firmness, its elasticity and/or its suppleness.

A subject-matter of the invention is thus a cosmetic or dermatological composition comprising a compound which comprises units (Ia) and (Ib) as defined below. In the continuation of the present description, these compounds are referred to as "hyaluronic acid derivatives".

The said hyaluronic acid derivatives form another subject-matter of the invention.

It has been found that the functionalization of hyaluronic acid by entities capable of forming four hydrogen bonds, more specifically the functionalization by ureidopyrimidones, makes it possible to solve the problem of enzymatic decomposition.

Furthermore, the mechanical properties of the derivatives thus prepared can be adjusted, in particular as a function of the degree of functionalization.

Hyaluronic acid belongs to the family of the glycosaminoglycans (GAGs). It is formed by the repetition of the hydrophilic disaccharide unit, in which sodium D-glucuronate and/or D-glucuronic acid is connected to N-acetylglucosamine via alternating β1-4 and β1-3 glycoside bonds or via β1-4 glycoside bonds alone. Under physiological conditions, this polysaccharide is found not in the acid form but in the form of a sodium salt, sodium hyaluronate.

Hyaluronic acid is understood to mean, in the present description, hyaluronic acid or one of its salts, in particular its sodium, potassium, magnesium and calcium salts.

Hyaluronic acid thus generally comprises repeat units of formula (Ia) as described above.

In the derivatives according to the invention, a portion of these units (Ia) has been functionalized by a group comprising a ureidopyrimidone unit of formula (I), which results in functionalized units corresponding to the formula (Ib) as described below.

The derivatives according to the invention thus comprise both units (Ia) and (Ib):

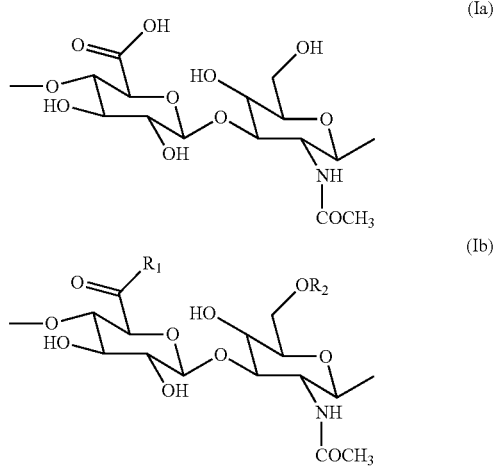

in which:
$R_1$ represents OH or an —NH—R'—Z radical,
$R_2$ represents H or a —C(O)—NH—R'—Z radical, with:
R' a linear or branched, divalent $C_1$-$C_{18}$, in particular $C_2$-$C_{14}$, indeed even $C_4$-$C_{10}$, alkyl radical; or a single bond;
Z a radical of formula (I):

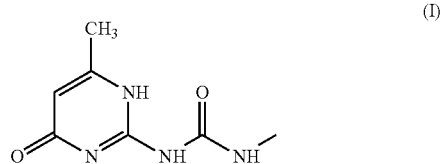

it being understood that at least one, preferably just one, of the $R_1$ and $R_2$ radicals comprises a Z radical.

Preferably, the ratio by weight of the units (Ia) to the units (Ib) is such that the degree of functionalization of the derivative is between 1% and 99%, better still between 1.5% and 60% and preferably between 2% and 30%.

Preferably, the derivatives according to the invention advantageously have an average molecular weight (Mw) of between 5000 and 3 000 000 daltons, better still between 50 000 and 2 500 000 daltons, indeed even between 500 000 and 2 000 000 daltons.

It should be remembered that the derivatives according to the invention can be provided in the form of salts, in particular sodium, ammonium or potassium salt.

The hyaluronic acid derivatives according to the invention have a very particular application in cosmetic or dermatological compositions.

They can be present in the said compositions, alone or as mixtures, in an amount ranging from 0.1% to 3% by weight, relative to the total weight of the composition, in particular from 0.5% to 2% by weight, indeed even from 0.8% to 1.5% by weight.

The cosmetic or dermatological compositions according to the invention moreover comprise a cosmetically or dermatologically acceptable medium, i.e. a medium that is compatible with keratin materials, such as the skin of the face or body, the lips, the hair, the eyelashes, the eyebrows and the nails.

The compositions according to the invention may be in any formulation form conventionally used, in particular for topical application, and in particular in the form of aqueous or aqueous/alcoholic solutions, of oil-in-water (O/W), water-in-oil (W/O) or multiple (triple: W/O/W or O/W/O) emulsions, of aqueous gels or of dispersions of a fatty phase in an aqueous phase using spherules, it being possible for these spherules to be polymeric nanoparticles, such as nanospheres and nanocapsules, or lipid vesicles of ionic and/or nonionic type (liposomes, niosomes or oleosomes), of nanoemulsions, or of thin films. These compositions are prepared according to the usual methods.

The compositions according to the invention may be more or less fluid and may have the appearance of a white or coloured cream, an ointment, a milk, a lotion, a serum, a paste or a foam. They can optionally be applied to the skin in the form of an aerosol. They can also be in solid form, for example in the form of a stick.

The composition according to the invention can in particular be provided in the form of a product for caring for or making up the skin of the face or body, the lips, the nails, the eyelashes, the eyebrows or the hair; of an aftershave gel or lotion; of a depilatory cream; of a body or hair hygiene composition, such as a shower gel, a shampoo, a soap or a cleansing bar; of a hair product, in particular for cleaning, styling, caring for, treating, repairing, dyeing or fixing the hair, such as a hair-setting lotion, a styling cream or gel, a dyeing composition, a hair-restructuring lotion, a permanent-wave composition, or a lotion or gel for combating hair loss; or of an oral composition.

The physiologically acceptable medium in which the compounds can be used, and also its constituents, their amounts, the formulation form of the composition and the preparation method thereof may be chosen by those skilled in the art on the basis of their general knowledge as a function of the type of composition desired. In particular, the composition may comprise any fatty substance normally used in the field of application envisaged. Mention may in particular be made of silicone fatty substances, such as silicone oils, gums and waxes, and also non-silicone fatty substances, such as oils, pastes and waxes of vegetable, mineral, animal and/or synthetic origin. The oils may optionally be volatile or non-volatile.

The composition may also comprise an aqueous medium that comprises water, an aqueous/alcoholic medium containing a $C_2$-$C_6$ alcohol such as ethanol or isopropanol, or an organic medium comprising standard organic solvents such as $C_2$-$C_6$ alcohols, in particular ethanol and isopropanol, glycols, such as propylene glycol, or ketones.

The composition according to the invention may also comprise the adjuvants that are customary in the cosmetic and dermatological fields, such as thickeners, emulsifiers, surfactants, gelling agents, cosmetic active agents, fragrances, fillers, colourants, moisturizing agents, vitamins or polymers. The amounts of these various adjuvants are those conventionally used in the fields under consideration, for example from 0.001% to 20% of the total weight of the composition. These adjuvants and the concentrations thereof must be such that they are not detrimental to the advantageous properties of the compositions according to the invention.

Another subject-matter of the invention is a cosmetic treatment method, especially for making up, caring for, cleaning or dyeing keratin materials, especially the skin of the body or face, the lips, the nails, the hair and/or the eyelashes, comprising the use, in particular the application to the said keratin materials, of a cosmetic composition as defined above.

Preferably, it is a cosmetic treatment method for reducing the signs of ageing of the skin and/or mucous membranes, in particular for reducing wrinkles and fine lines and/or for restoring the volume thereof to the face or body.

The invention is illustrated in greater detail in the examples that follow.

EXAMPLE 1

The procedure used for the synthesis is that described in WO2000/016818 and represented below:

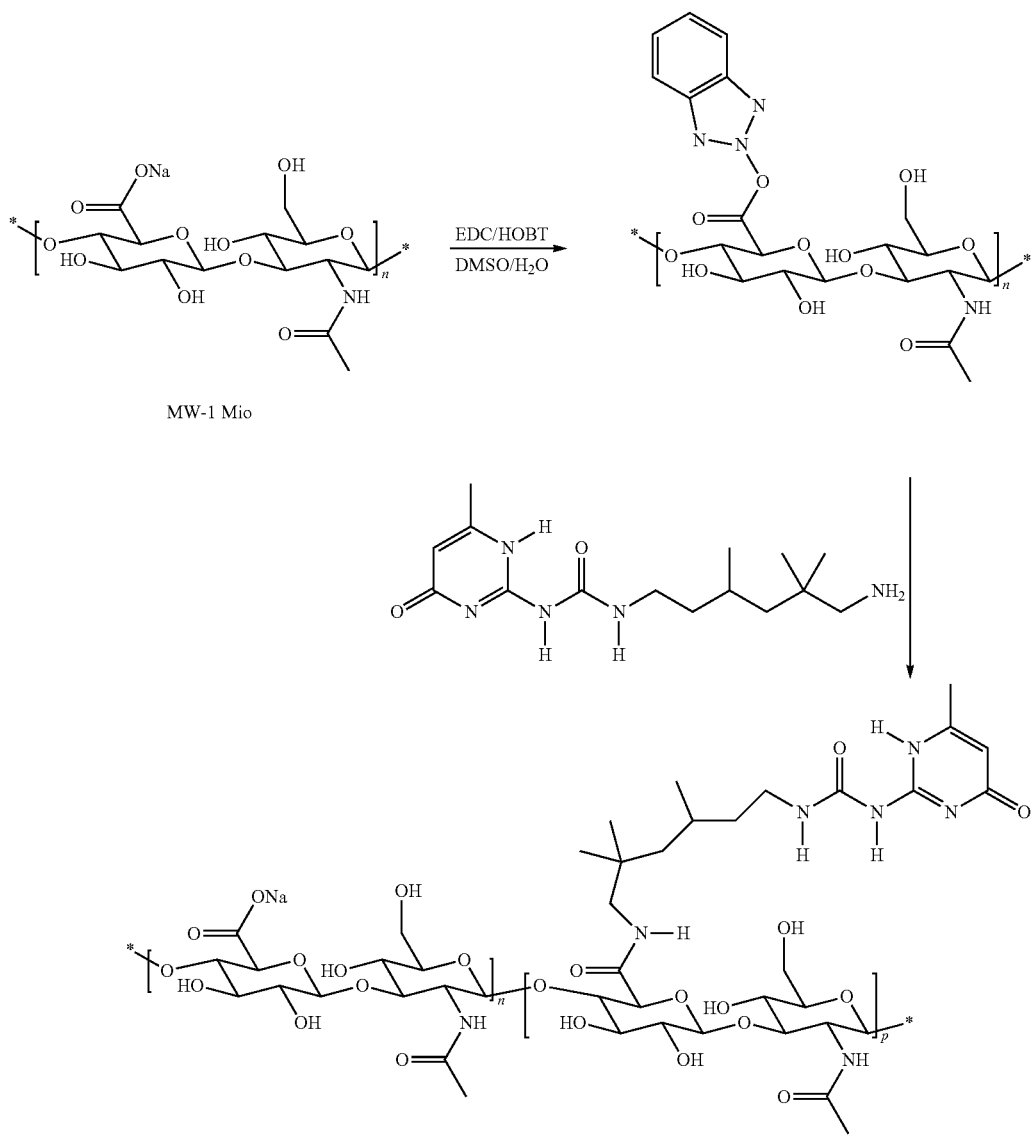

MW-1 Mio 10 ml of 1,6-diamino-2,2,4-trimethylhexane are added to 2.1 g of imidazole-functionalized ureidopyrimidone (supplied by SupraPolix), followed by stirring under a controlled atmosphere at ambient temperature for 30 minutes. After addition of diethyl ether, a white precipitate is obtained, which precipitate is filtered off and then re-dissolved in chloroform, followed by a second precipitation from diethyl ether.

The white precipitate is dried under vacuum and used as is for the functionalization of the hyaluronic acid.

1 g of sodium hyaluronate is dissolved in 170 ml of water. 0.923 g of the amine-functionalized ureidopyrimidone dendron obtained above, in solution in 170 ml of anhydrous DMSO, is added thereto. The solution is mixed at ambient temperature and the pH is adjusted to 6.8 by addition of a 0.1 M NaOH solution.

1.34 g of 1-hydroxybenzotriazole (HOBt) are dissolved in 5 ml of DMSO and are added to the reaction mixture, followed by the addition of 1.91 g of 1-ethyl-3-(3-(dimethylamino)propyl)carbodiimide. After stirring, the pH of the solution is maintained at 6.8 by addition of a 0.1M NaOH solution, until the pH has stabilized. The pH is subsequently brought to 7, and 15 g of an aqueous NaCl solution are added. The reaction mixture is subsequently precipitated from 4 liters of an ethanol/water (4 v/1 v) mixture and left standing overnight. The mixture is subsequently filtered and the filter residue is rinsed four times with an ethanol/water (4 v/1 v) mixture, followed by two rinsing operations with 200 ml of an ethanol/water (9 v/1 v) mixture, and finally with 200 ml of ethanol.

The desired product is obtained in the form of a white solid which is dried under vacuum at 40° C. (yield: 89%).

EXAMPLE 2

Synthesis from Hyaluronic Acid in the Sodium Salt Form

The general procedure is represented below:

0.5 g of sodium hyaluronate (polymer with repetitions of sugar rings $C_{14}H_{20}NO_{11}Na$, FW=401) is dissolved in 400 ml of water and elution is carried out on a Dowex 50x2-200 (13G, 4.8 meq/G resin) ion-exchange column. The pH of the viscous sodium hyaluronate solution changes from an initial value of approximately 6 to 3-4. The resulting hyaluronic acid solution is neutralized with a 40% tetrabutylammonium hydroxide solution in order to have, in the end, a solution with a pH in the vicinity of 6-7. The solution is lyophilized and makes it possible to quantitatively obtain the hyaluronic acid in its $O^-NBu_4^+$ form.

0.2 g of the salt thus obtained is dissolved in 10 ml of DMSO and the isocyanate-functionalized ureidopyrimidone dendron (supplied by SupraPolix) below is added to the solution:

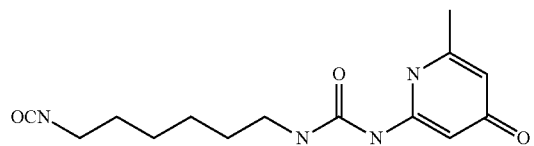

The molar ratio is adjusted as a function of the degree of functionalization desired for the hyaluronic acid. A drop of dibutyltin dilaurate catalyst is added to the reaction mixture. The viscous solution is heated to 70° C. and stirring is maintained for 12 hours under a controlled atmosphere. The reaction is monitored by infrared is spectroscopy with disappearance of the peak characteristic of the isocyanates. Once the reaction has stopped, the reaction mixture is dissolved in 10 ml of DMSO and filtered through celite. The resulting solution is precipitated dropwise from 200 ml of a diethyl ether/THF (1 v/1 v) mixture, and the white solid thus recovered is washed with a diethyl ether/THF (5 v/3 v) mixture and then a diethyl ether/THF (3 v/1 v) mixture. The yield varies between 50% and 100% as a function of the degree of functionalization. In order to make sure that the ureidopyrimidone dendron

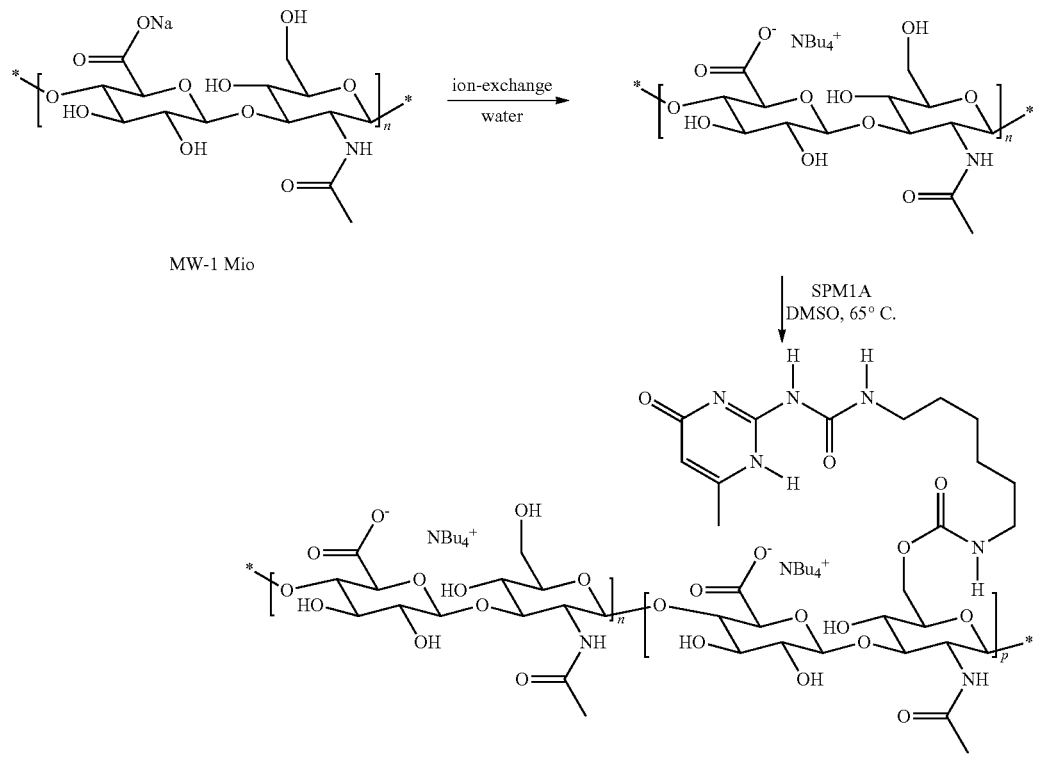

has completely reacted, 1 ml of the resulting solution can be withdrawn and dissolved in 1 ml of water: a clear solution guarantees that the dendron has completely reacted.

In order to obtain the hyaluronic acid in its sodium salt form, 60 mg of the powder obtained above are dissolved in 10 ml of water, stirring being maintained overnight. After two successive dialyses in a saline NaCl solution, followed by three dialyses in water, the aqueous solution is lyophilized and makes it possible to obtain the desired product in the form of a white powder.

EXAMPLE 3

Comparative Test

Reactants:
  test buffer: 0.1M phosphate buffer, pH=5.3
  hyaluronic acid prepared at 1.2 mg/ml (2×) as test buffer
  hyaluronidase (Sigma type IV-S, H3884) prepared at 1 mg/ml (3×) in test buffer
  bovine albumin BSA (Sigma A7888) prepared at 1% in 0.5M acetate buffer, pH=4.2

The compounds of Examples 1 and 2 are brought together with the enzyme and preincubated over ice for 10 minutes 5 concentrations of product are tested, and the treatments are carried out in n=3. At the end of the preincubation, the hyaluronic acid was added and the mixture was incubated at 37° C. for 60 minutes before precipitating the hyaluronic acid with a BSA solution.

The absorption (OD) at 540 nm was measured using a plate reader (Thermomax, Molecular Devices).

It is found that the compounds of Examples 1 and 2 are not hyaluronidase substrates; they are not decomposed by the enzyme, in contrast to the native hyaluronic acid.

The invention claimed is:

1. A cosmetic or dermatological composition comprising a hyaluronic acid compound formed by the repetition of the hydrophilic disaccharide unit, in which sodium D-glucuronate and/or D-glucuronic acid is connected to N-acetylglucosamine via alternating β1-4 and β1-3 glycoside bonds or via β1-4 glycoside bonds alone, which comprises units (Ia) and units (Ib), or one of its salts:

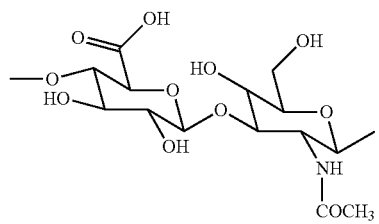

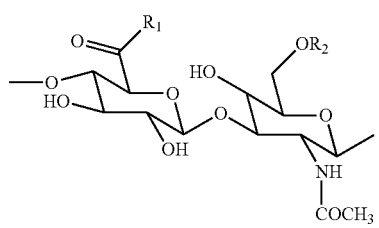

in which:
  $R_1$ represents OH or an —NH—R'—Z radical,
  $R_2$ represents H or a —C(O)—NH—R'—Z radical, with:
  R' being a linear or branched, divalent $C_1$-$C_{18}$ alkyl radical; or a single bond;
  Z being a radical of formula (I):

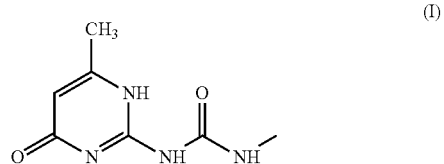

wherein at least one of the $R_1$ and $R_2$ radicals comprises a Z radical.

2. The composition according to claim 1, in which the degree of functionalization of the compound is between 1.5% and 60%.

3. The composition according to claim 1, in which the compound is present, alone or as mixtures, in an amount ranging from 0.1% to 3% by weight, relative to the total weight of the composition.

4. The composition according to claim 1, which is provided in the form of a product for caring for or making up the skin of the face or body, the lips, the nails, the eyelashes, the eyebrows or the hair; of an aftershave gel or lotion; of a depilatory cream; of a body or hair hygiene composition, a soap or a cleansing bar; of a hair product, in particular for cleaning, styling, caring for, treating, repairing, dyeing or fixing the hair, a dyeing composition, a hair-restructuring lotion, a permanent-wave composition, or a lotion or gel for combating hair loss; or of an oral composition.

5. The composition according to claim 1, comprising at least one ingredient chosen from silicone fatty substances, non-silicone fatty substances, water, a $C_2$-$C_6$ alcohol; glycols; thickeners, emulsifiers, surfactants, gelling agents, cosmetic active agents, fragrances, fillers, colourants, moisturizing agents, vitamins or polymers.

6. A cosmetic treatment method comprising applying a cosmetic composition as defined in claim 1 to a keratin material.

7. The method according to claim 6, characterized in that it is a cosmetic treatment method for reducing the signs of ageing of the skin and/or mucous membrane, which comprises applying said cosmetic composition to the skin and/or mucous membrane.

8. A hyaluronic acid compound formed by the repetition of the hydrophilic disaccharide unit, in which sodium D-glucuronate and/or D-glucuronic acid is connected to N-acetylglucosamine via alternating β1-4 and β1-3 glycoside bonds or via β1-4 glycoside bonds alone, which comprises units (Ia) and (Ib), or one of its salts:

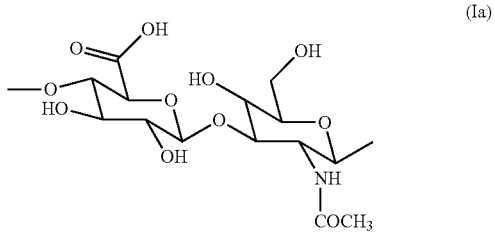

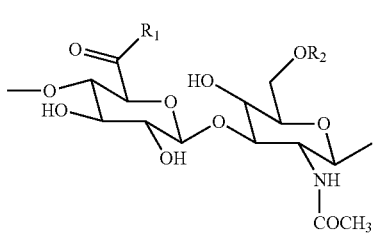

in which:
R₁ represents OH or an —NH—R'—Z radical,
R₂ represents H or a —C(O)—NH—R'—Z radical,
with:
R' being a linear or branched, divalent $C_1$-$C_{18}$ alkyl radical; or a single bond;
Z being a radical of formula (I):

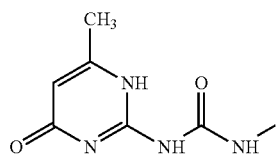

wherein at least one of the R₁ and R₂ radicals comprises a Z radical.

9. The derivative according to claim 8, in which the degree of functionalization of the compound is between 1.5% and 60%.

10. The composition according to claim 1, in which the compound is present, alone or as mixtures, in an amount ranging from 0.5% to 2% by weight relative to the total weight of the composition.

11. The composition according to claim 2, which is provided in the form of a product for caring for or making up the skin of the face or body, the lips, the nails, the eyelashes, the eyebrows or the hair; of an aftershave gel or lotion; of a depilatory cream; of a body or hair hygiene composition, a soap or a cleansing bar; of a hair product, in particular for cleaning, styling, caring for, treating, repairing, dyeing or fixing the hair, a dyeing composition, a hair-restructuring lotion, a permanent-wave composition, or a lotion or gel for combating hair loss; or of an oral composition.

12. The composition according to claim 3, which is provided in the form of a product for caring for or making up the skin of the face or body, the lips, the nails, the eyelashes, the eyebrows or the hair; of an aftershave gel or lotion; of a depilatory cream; of a body or hair hygiene composition, a soap or a cleansing bar; of a hair product, in particular for cleaning, styling, caring for, treating, repairing, dyeing or fixing the hair, a dyeing composition; a hair-restructuring lotion, a permanent-wave composition, or a lotion or gel for combating hair loss; or of an oral composition.

13. The composition according to claim 2, comprising at least one ingredient chosen from silicone fatty substances, non-silicone fatty substances, water, a $C_2$-$C_6$ alcohol; glycols; thickeners, emulsifiers, surfactants, gelling agents, cosmetic active agents, fragrances, fillers, colourants, moisturizing agents, vitamins or polymers.

14. The composition according to claim 3, comprising at least one ingredient chosen from silicone fatty substances, non-silicone fatty substances, water, a $C_2$-$C_6$ alcohol; glycols; thickeners, emulsifiers, surfactants, gelling agents, cosmetic active agents, fragrances, fillers, colourants, moisturizing agents, vitamins or polymers.

15. The composition according to claim 4, comprising at least one ingredient chosen from silicone fatty substances, non-silicone fatty substances, water, a $C_2$-$C_6$ alcohol; glycols; thickeners, emulsifiers, surfactants, gelling agents, cosmetic active agents, fragrances, fillers, colourants, moisturizing agents, vitamins or polymers.

16. A cosmetic treatment method comprising applying a cosmetic composition as defined in claim 2 to a keratin material.

17. A cosmetic treatment method comprising applying a cosmetic composition as defined in claim 3 to a keratin material.

18. A cosmetic treatment method comprising applying a cosmetic composition as defined in claim 4 to a keratin material.

19. A cosmetic treatment method comprising applying a cosmetic composition as defined in claim 5 to a keratin material.

20. The composition according to claim 10, which is provided in the form of a product for caring for or making up the skin of the face or body, the lips, the nails, the eyelashes, the eyebrows or the hair; of an aftershave gel or lotion; of a depilatory cream; of a body or hair hygiene composition, a soap or a cleansing bar; of a hair product, in particular for cleaning, styling, caring for, treating, repairing, dyeing or fixing the hair, a dyeing composition, a hair-restructuring lotion, a permanent-wave composition, or a lotion or gel for combating hair loss; or of an oral composition.

21. The composition according to claim 1, in which the degree of functionalization of the compound is between 2% and 30%.

22. The compound according to claim 8, in which the degree of functionalization of the derivative is between 2% and 30.

23. The composition according to claim 1, in which the compound is present, alone or as mixtures, in an amount ranging from 0.8% to 1.5% by weight relative to the total weight of the composition.

24. The compound according to claim 8, wherein the average molecular weight of is between 5000 and 3 000 000 daltons.

* * * * *